(12) United States Patent
Kim et al.

(10) Patent No.: US 10,517,683 B2
(45) Date of Patent: Dec. 31, 2019

(54) PARALLEL-TYPE MICRO ROBOT AND SURGICAL ROBOT SYSTEM HAVING THE SAME

(71) Applicants: Sung-Mok Kim, Seoul (KR); Whee-Kuk Kim, Seoul (KR); Byung-Ju Yi, Bucheon-si (KR)

(72) Inventors: Sung-Mok Kim, Seoul (KR); Whee-Kuk Kim, Seoul (KR); Byung-Ju Yi, Bucheon-si (KR)

(73) Assignees: KOH YOUNG TECHNOLOGY INC., Seoul (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 426 days.

(21) Appl. No.: 15/323,261

(22) PCT Filed: Jun. 30, 2015

(86) PCT No.: PCT/KR2015/006728
§ 371 (c)(1),
(2) Date: Dec. 30, 2016

(87) PCT Pub. No.: WO2016/003172
PCT Pub. Date: Jan. 7, 2016

(65) Prior Publication Data
US 2018/0185102 A1  Jul. 5, 2018

(30) Foreign Application Priority Data

Jun. 30, 2014  (KR) .................. 10-2014-0080661

(51) Int. Cl.
*A61B 34/30* (2016.01)
*B25J 7/00* (2006.01)
(Continued)

(52) U.S. Cl.
CPC .............. *A61B 34/30* (2016.02); *A61B 17/00* (2013.01); *A61B 34/70* (2016.02); *B23Q 1/5462* (2013.01);
(Continued)

(58) Field of Classification Search
CPC . B25J 7/00; B25J 9/0072; B25J 9/0063; B25J 9/0096; B25J 9/046; B25J 9/023;
(Continued)

(56) References Cited

U.S. PATENT DOCUMENTS 5,308,352 A * 5/1994 Koutrouvelis ..... A61B 17/3403
604/116
5,340,247 A * 8/1994 Cuneo .................... B23Q 1/626
144/134.1
(Continued)

FOREIGN PATENT DOCUMENTS

JP  2007-520361  7/2007
KR  20-0305531  3/2003
(Continued)

OTHER PUBLICATIONS

International Search Report for International Application No. PCT/KR2015/006728, dated Aug. 19, 2015.

*Primary Examiner* — Luis A Gonzalez
(74) *Attorney, Agent, or Firm* — Kile Park Reed & Houtteman PLLC

(57) ABSTRACT

A parallel-type micro robot capable of precise control while minimizing size thereof and a surgical robot system having the same are disclosed. The parallel-type micro robot includes a base plate, a work plate, a main fixing shaft module, a horizontal movement module and at least one angle-controlling module. The base plate includes a base body portion and at least one base connecting portion connected to the base body portion. The work plate includes (Continued)

a work body portion corresponding to the base body portion and at least one work connecting portion connecting to the work body portion to correspond to the base connecting portion. The main fixing shaft module is disposed between the base body portion and the work body portion, and coupled to the work body portion such that the work body portion is rotatable. The horizontal movement module is disposed between the main fixing shaft module and the base body portion, and moves the main fixing shaft module along first and second directions intersecting each other. The angle-controlling module is coupled to the base connecting portion such that the base connecting portion is rotatable, is coupled to the work connecting portion such that the work connecting portion is rotatable, and allows translational motion between the base connecting portion and the work connecting portion. Thus, a size of a robot may be minimized while improving the structural stability and precise control.

15 Claims, 10 Drawing Sheets

(51) Int. Cl.
| | | |
|---|---|---|
| *B25J 17/00* | (2006.01) | |
| *A61B 34/00* | (2016.01) | |
| *B25J 9/00* | (2006.01) | |
| *B23Q 1/54* | (2006.01) | |
| *B25J 5/02* | (2006.01) | |
| *A61B 17/00* | (2006.01) | |
| *B25J 9/04* | (2006.01) | |
| *B25J 9/02* | (2006.01) | |

(52) U.S. Cl.
CPC . *B25J 5/02* (2013.01); *B25J 7/00* (2013.01); *B25J 9/0063* (2013.01); *B25J 9/0072* (2013.01); *B25J 9/046* (2013.01); *A61B 2017/00345* (2013.01); *A61B 2034/304* (2016.02); *B25J 9/0096* (2013.01); *B25J 9/023* (2013.01); *Y10S 901/17* (2013.01)

(58) Field of Classification Search
CPC . B25J 17/0266; B25J 17/0216; B23Q 1/5462; A61B 2034/304; A61B 34/70; A61B 34/30
See application file for complete search history.

(56) References Cited

U.S. PATENT DOCUMENTS

| | | | |
|---|---|---|---|
| 6,330,837 B1 * | 12/2001 | Charles | B25J 11/00 74/490.06 |
| 6,808,344 B2 * | 10/2004 | Chen | B23Q 1/5462 409/201 |
| 2004/0126198 A1 | 7/2004 | Chen | |
| 2015/0040711 A1 * | 2/2015 | Kim | B25J 7/00 74/490.01 |

FOREIGN PATENT DOCUMENTS

| | | | |
|---|---|---|---|
| KR | 10-1119512 | 2/2012 | |
| KR | 10-2013-0120971 | 11/2013 | |
| KR | 10-2013-0139086 | 12/2013 | |
| WO | WO-03086717 A1 * | 10/2003 | B23Q 1/012 |
| WO | 2005/074368 | 8/2005 | |

* cited by examiner

PARALLEL-TYPE MICRO ROBOT AND SURGICAL ROBOT SYSTEM HAVING THE SAME

TECHNICAL FIELD

The present invention relates to a parallel-type micro robot and a surgical robot system having the same, and more particularly, the present invention relates to a parallel-type micro robot and a surgical robot system having the same precisely positioning a surgical instrument at a desired location.

BACKGROUND ART

Generally, in order to control the position and posture on a three-dimensional plane, a robot with a serial structure has been widely used in surgery using a robot. However, recently, various kinds of parallel-structured robots have been developed and used in contrast to the serial structure.

Such a parallel-structured surgical robot has various advantages over a serial-structured surgical robot. The first advantage is that the inertia mass of the moving part is reduced as compared with the serial-type surgical robot, thereby increasing speed and acceleration of a machine. A second advantage is that a base platform and a moving platform are connected by a plurality of actuators, so that each of the actuators receives only tensile and compressive forces instead of bending forces, thereby increasing mechanical stiffness. The third advantage is that error of each of the actuators is reflected on the moving platform on average, so that accuracy is improved compared with a serial-type surgical robot in which errors are accumulated.

However, when a degree of freedom of the general parallel-structured surgical robot is increased, the number of actuators corresponding to the increased degree of freedom is required to be installed between the base platform and the moving platform. Thus, when parallel-structured robots with more than 4 degrees of freedom are manufactured with the increase of manufacturing cost, the size of the robots may be increased, which may cause a problem of being limited in installation and operation space. In addition, when a strong load is applied to an actuator disposed between the base platform and the moving platform, especially an actuator for translational motion, the structural stability may be adversely affected.

DETAILED DESCRIPTION OF THE INVENTION

Objects of the Invention

Thus, the present invention has been provided to solve the above problems. An object of the present invention is to provide a parallel-type micro robot capable of improving structural stability while minimizing the size and precisely controlling the robot. In addition, another object of the present invention is to provide a surgical robot system having the parallel-type micro robot.

Technical Solution

In an exemplary embodiment of the present invention, a parallel-type micro robot includes a base plate, a work plate, a main fixing shaft module, a horizontal movement module, and at least one angle-controlling module.

The base plate includes a base body portion and at least one base connecting portion connected to the base body portion. The work plate includes a work body portion corresponding to the base body portion and at least one work connecting portion connecting to the work body portion to correspond to the base connecting portion. The main fixing shaft module is disposed between the base body portion and the work body portion, and coupled to the work body portion such that the work body portion is rotatable. The horizontal movement module is disposed between the main fixing shaft module and the base body portion, and moves the main fixing shaft module along first and second directions intersecting each other. The angle-controlling module is coupled to the base connecting portion such that the base connecting portion is rotatable, is coupled to the work connecting portion such that the work connecting portion is rotatable, and allows translational motion between the base connecting portion and the work connecting portion.

The base connecting portion may include first and second base connecting portions connected to the base body portion, and the work connecting portion may include first and second work connecting portions connected to the work body portion to correspond to the first and second base connecting portions, respectively. The angle-controlling module may include a first angle-controlling module and a second angle-controlling module. The first angle-controlling module is coupled to the first base connecting portion such that the first base connecting portion is rotatable, is coupled to the first work connecting portion such that the first work connecting portion is rotatable, and allows translational motion between the first base connecting portion and the first work connecting portion. The second angle-controlling module is coupled to the second base connecting portion such that the second base connecting portion is rotatable, is coupled to the second work connecting portion such that the second work connecting portion is rotatable, and allows translational motion between the second base connecting portion and the second work connecting portion.

The first base connecting portion may be connected to the base body portion in one direction of the first and second directions, and the second base connecting portion may be connected to the base body portion in the other direction of the first and second directions. The first work connecting portion may be connected to the work body portion in the one direction, and the second work connecting portion may be connected to the work body portion in the other direction.

The first and second directions may perpendicularly intersect each other.

The work plate may further include a mount connecting portion connected to the work body portion and providing a mount space.

The mount connecting portion may be disposed at a location corresponding to the work connecting portion.

The parallel-type micro robot may further include a surgical mount coupled to the mount connecting portion, and a surgical unit is mountable on the surgical mount.

The angle-controlling module may include a translational motion unit allowing translational motion between the base connecting portion and the work connecting portion, a one-side rotational motion connecting unit connecting the base connecting portion and the translational motion unit to allow rotational motion of the base connecting portion, and an another-side rotational motion connecting unit connecting the work connecting portion and the translational motion unit to allow rotational motion of the work connecting portion.

The angle-controlling module may further include an up-down movement guide unit coupled to the translational motion unit to guide translational motion according to the translational motion unit.

The translational motion unit may include an up-down movement actuator providing power for translational motion, and an up-down moving shaft portion performing translational motion according to the power of the up-down movement actuator between the work connecting portion and the up-down movement actuator, or between the base connecting portion and the up-down movement actuator.

The up-down movement guide unit may include a guide body portion coupled to the up-down moving shaft portion to perform translational motion with the up-down moving shaft portion, and an up-down movement sliding portion disposed between the up-down movement actuator and the guide body portion to slide and guide the guide body portion when the guide body portion performs translational motion.

The translational motion unit may further include an actuator mounting portion having an inner face on which the up-down movement actuator is mounted and an outer face coupled to the up-down movement sliding portion.

The up-down movement sliding portion may include an up-down movement rail portion coupled to one of the up-down movement actuator and the guide body portion, and an up-down movement rail groove portion coupled to the other of the up-down movement actuator and the guide body portion to slide along the up-down movement rail portion.

The horizontal movement module may include a first sliding module disposed between the main fixing shaft module and the base body portion to move the main fixing shaft module along one direction of the first and second directions, and a second sliding module disposed between the main fixing shaft module and the first sliding module to move the main fixing shaft module along the other direction of the first and second directions.

The main fixing shaft module may include a main fixing shaft unit coupled to the horizontal movement module to be moved along the first and second directions by the horizontal movement module, and a main rotational motion connecting unit connecting the main fixing shaft unit and the work body portion to allow rotational motion of the work body portion.

In an exemplary embodiment of the present invention, a surgical robot system includes a parallel-type micro robot and a robot installation stage on which the parallel-type micro robot is installed corresponding to an operating table on which a patient is disposed.

The parallel-type micro robot includes a base plate, a work plate, a main fixing shaft module, a horizontal movement module, and at least one angle-controlling module.

The base plate is installed on the robot installation stage, and includes a base body portion and at least one base connecting portion connected to the base body portion. The work plate includes a work body portion corresponding to the base body portion and at least one work connecting portion connecting to the work body portion to correspond to the base connecting portion. The main fixing shaft module is disposed between the base body portion and the work body portion, and coupled to the work body portion such that the work body portion is rotatable. The horizontal movement module is disposed between the main fixing shaft module and the base body portion, and moves the main fixing shaft module along first and second directions intersecting each other. The angle-controlling module is coupled to the base connecting portion such that the base connecting portion is rotatable, is coupled to the work connecting portion such that the work connecting portion is rotatable, and allows translational motion between the base connecting portion and the work connecting portion.

The robot installation stage may include a robot-installed part on which the parallel-type micro robot is installed, a one-directional moving part coupled to the robot-installed part to move the robot-installed part in one-direction crossing over the operating table, and a pair of another-directional moving parts respectively disposed at both sides of the operating table to be coupled to the one-directional moving part, to move the one-directional moving part along another-direction intersecting the one-direction.

Advantageous Effects

According to a parallel-type micro robot and a surgical robot system having the is parallel-type micro robot of the present invention, the parallel-type micro robot includes the first sliding module, the second sliding module, the first angle-controlling module and the second angle-controlling module, and controls translational motion in four directions. Thus, it is possible to implement a parallel-type micro robot having four degrees of freedom to precisely control the angle and position of the work plate.

In addition, by controlling the angle of the work plate using the first angle-controlling module and the second angle-controlling module, the number of actuators for controlling the angle of the work plate may be greatly reduced as compared with the conventional parallel-type micro robot, and as a result, it is possible to manufacture a small-sized, lightweight structure, thereby minimizing restrictions on installation and operation space.

Further, since each of the first and second angle-controlling modules has an up-down movement guide unit coupled to an up-down moving shaft portion, translational motion according to the up-down moving shaft portion may be stably guided. In other words, it may be structurally unstable during translational motion since the up-down moving shaft portion is relatively thin, but the up-down movement guide unit may enhance the structural stability by reinforcing the up-down moving shaft portion.

MODE FOR INVENTION

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art.

It will be understood that, although the terms first, second, third etc. may be used herein to describe various elements, components, regions, layers and/or sections, these elements, components, and/or sections should not be limited by these terms. These terms are only used to distinguish one element, component, region, layer or section from another region, layer or section. Thus, a first element, component, or section discussed below could be termed a second element, component, or section without departing from the teachings of the present invention.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs.

It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, preferred embodiments of the present invention will be described in detail with reference to the drawings.

Figure 1:
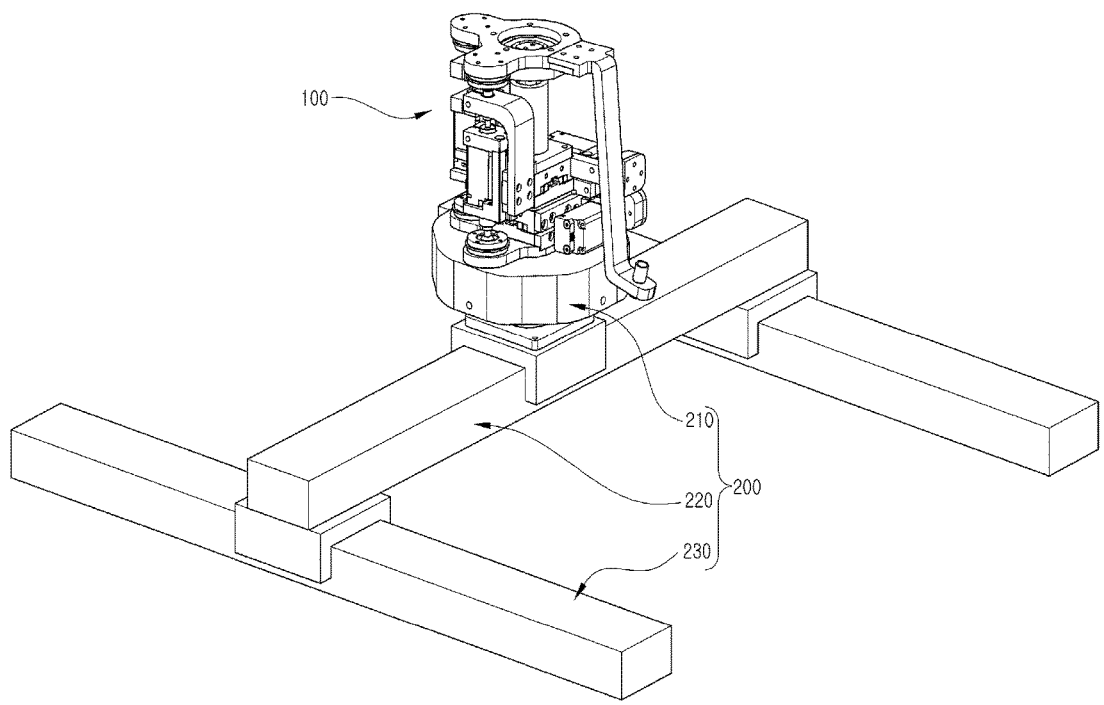
FIG. 1 is a perspective view illustrating a surgical robot system according to an exemplary embodiment of the present invention.

FIG. 1 is a perspective view illustrating a surgical robot system according to an exemplary embodiment of the present invention.

Referring to FIG. 1, a surgical robot system according to the present embodiment includes a parallel-type micro robot 100 on which a surgical unit (not shown) is mounted on, and a robot installation stage 200 on which a parallel-type micro robot 100 is installed corresponding to an operating table (not shown) on which a patient is disposed.

The robot installation stage 200 may move the parallel-type micro robot 100 along a horizontal direction substantially parallel to the operating table, while mounting and fixing the parallel-type micro robot 100. For example, the robot installation stage 200 may include a robot-installed part 210, a one-directional moving part 220, and a pair of another-directional moving parts 230.

The parallel-type micro robot 100 is installed on and fixed to the robot-installed part 210. Herein, the robot-installed part 210 may adjust a distance between the operating table and the parallel-type micro robot 100 by moving the parallel-type micro robot 100 along a vertical direction substantially perpendicular to the horizontal direction.

The one-directional moving part 220 is disposed along one-direction, or width direction, crossing over the operating table. The one-directional moving part 220 may be coupled to the robot-installed part 210 on an upper face, and move the robot-installed part 210 along the one-direction. As a result, the one-directional moving part 220 may determine a position of the parallel-type micro robot 100 in the one-direction.

The another-directional moving parts 230 are disposed on both sides of the operating table, respectively, along another-direction crossing the one-direction, for example, along the length direction of the operating table. Each of the another-directional moving parts 230 is coupled to the one-directional moving part 220 on the top surface thereof and moves the one-directional moving part 220 along the another-direction. As a result, the another-directional moving parts 230 may determine the position of the parallel-type micro robot 100 in the another-direction.

Thus, the surgical robot system may move the parallel-type micro robot 100 along the width and length directions of the operating table to determine a surgical position by the surgical unit mounted on the parallel-type micro robot 100. For example, the surgical robot system may be a surgical system that places the surgical unit on a desired portion of the patient's spine disposed on the operating table to perform surgery.

Hereinafter, the parallel-type micro robot 100 will be described in detail.

Figure 2:
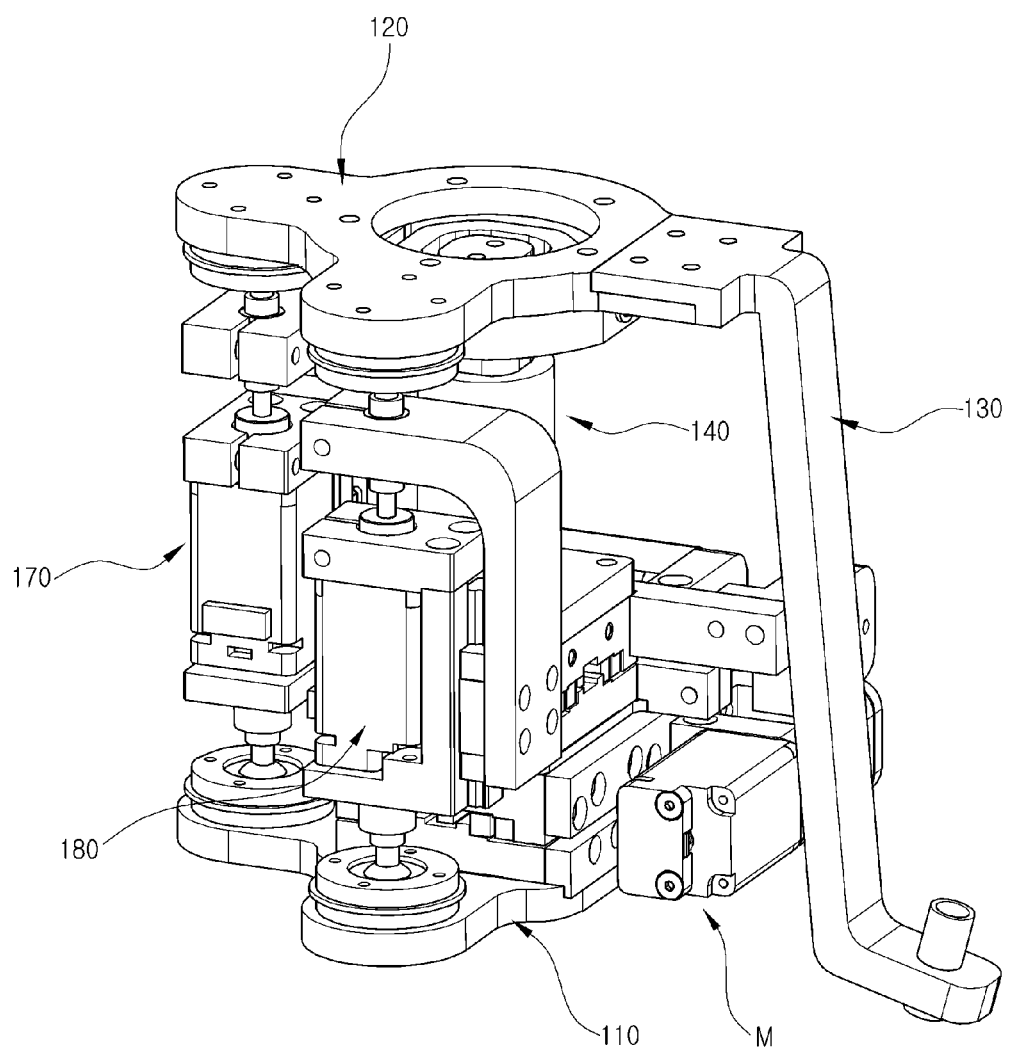
FIG. 2 is an enlarged perspective view of a parallel-type micro robot of the surgical robot system in FIG. 1.
Figure 3:
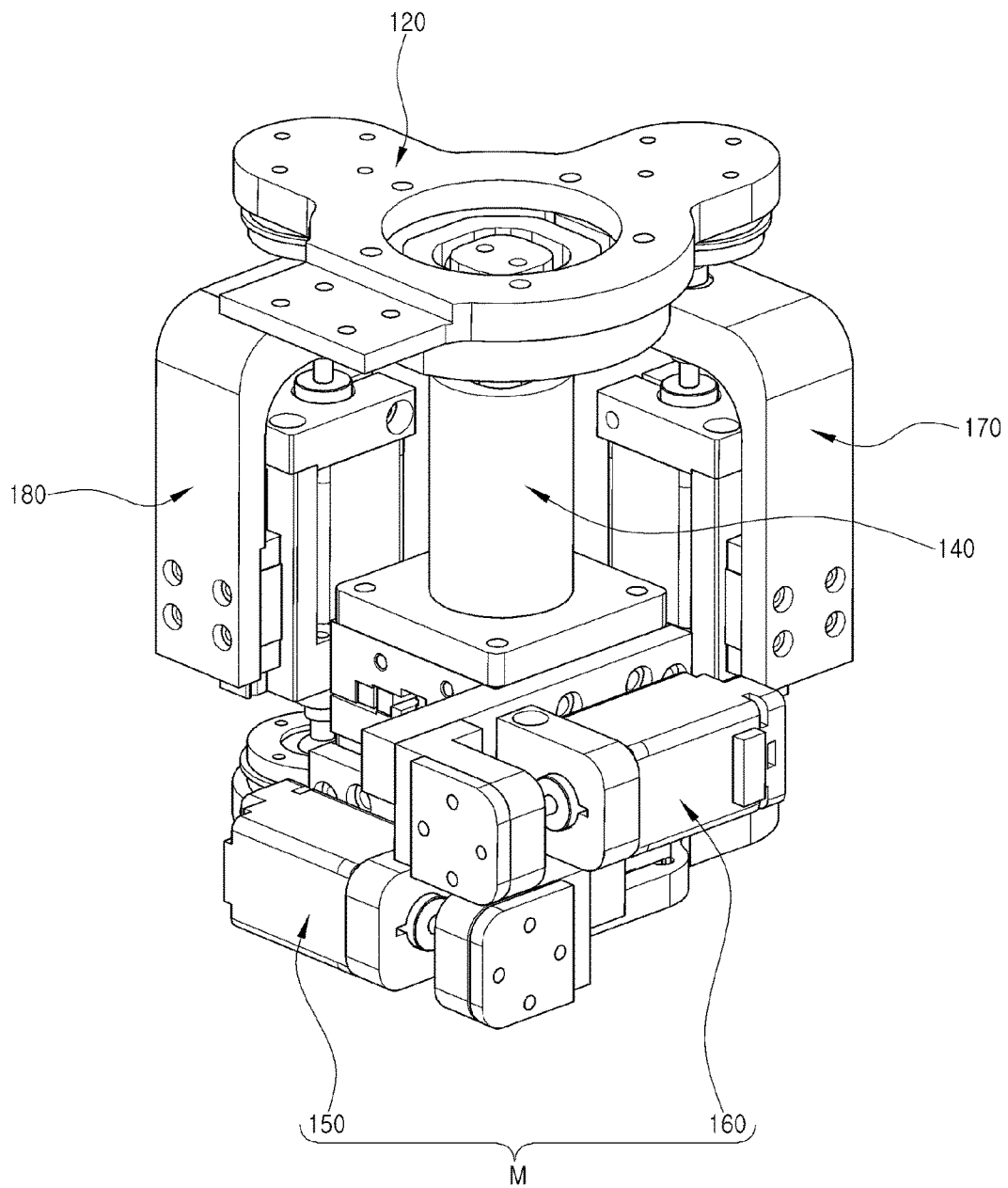
FIG. 3 is a perspective view showing a state in which a surgical mount is removed from the parallel-type micro robot in FIG. 2 from a different angle.
Figure 4:
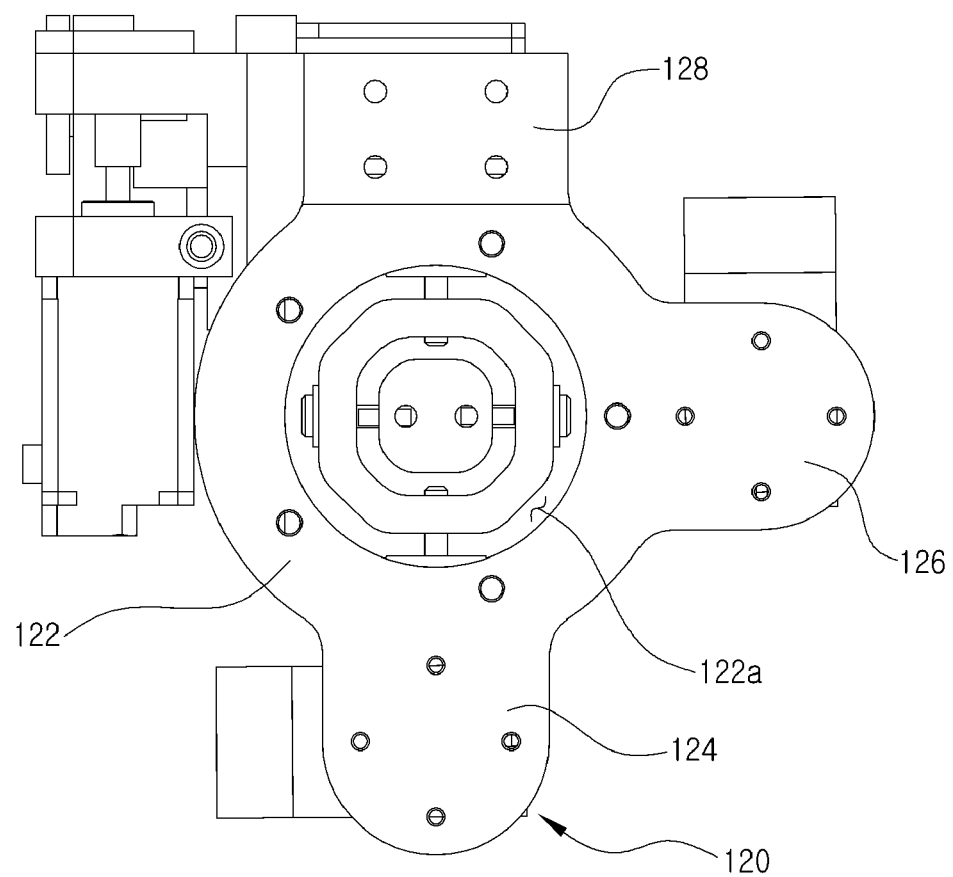
FIG. 4 is a plan view showing a parallel-type micro robot in FIG. 2 viewed from an upper side.
Figure 5:
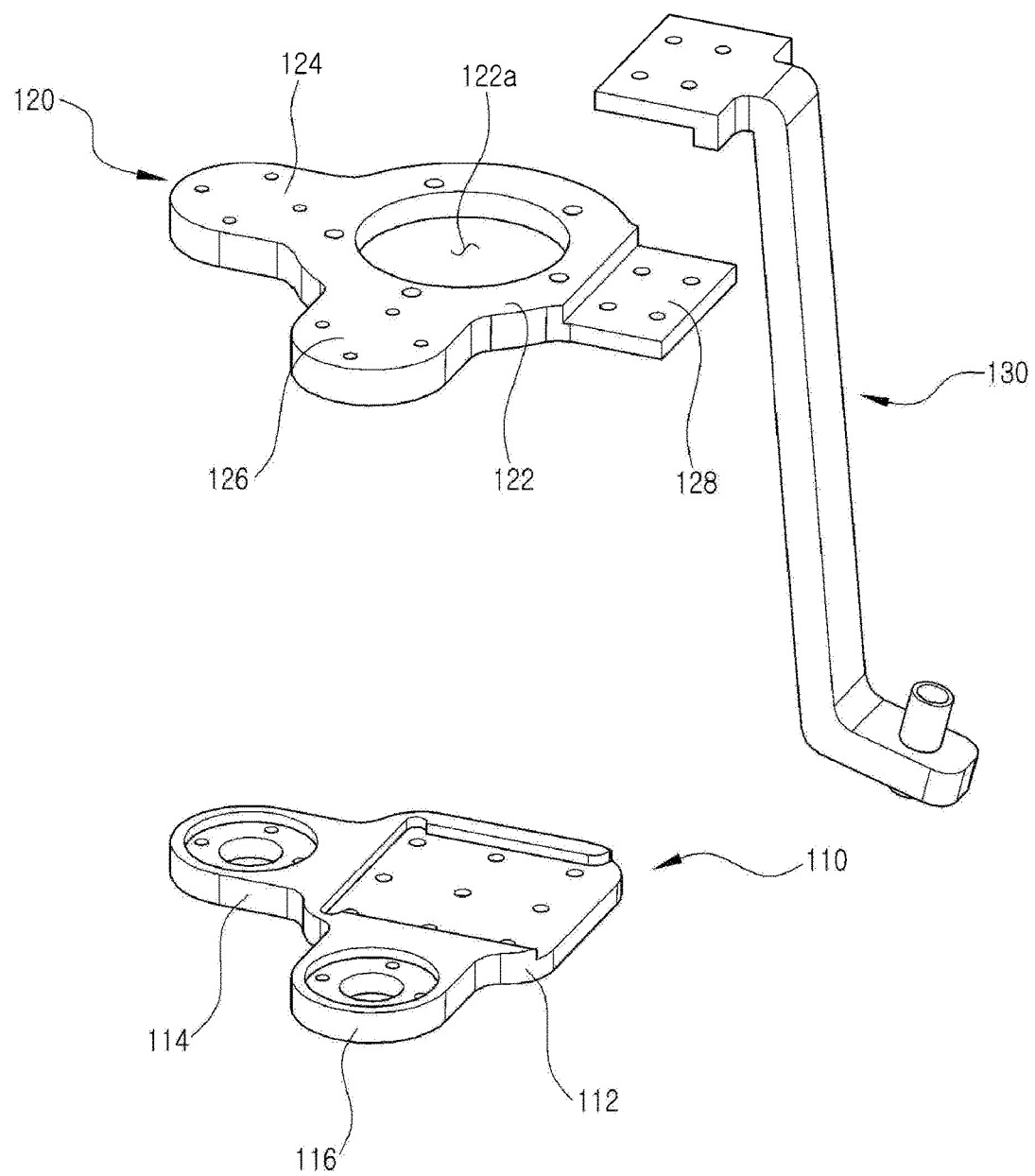
FIG. 5 is a perspective view illustrating a base plate, a work plate, and a surgical mount of the parallel-type micro robot in FIG. 2.

FIG. 2 is an enlarged perspective view of a parallel-type micro robot of the surgical robot system in FIG. 1. FIG. 3 is a perspective view showing a state in which a surgical mount is removed from the parallel-type micro robot in FIG. 2 from a different angle. FIG. 4 is a plan view showing a parallel-type micro robot in FIG. 2 viewed from an upper side. FIG. 5 is a perspective view illustrating a base plate, a work plate, and a surgical mount of the parallel-type micro robot in FIG. 2.

Referring to FIGS. 2 to 5, the parallel-type micro robot 100 may include a base plate 110, a work plate 120, a surgical mount 130, a main fixing shaft module 140, a horizontal movement module M, and an at least one angle-controlling module.

The base plate 110 is mounted on the robot-installed part 210 shown in FIG. 1. Particularly, the base plate 110 may include a base body portion 112 and at least one base connecting portion connected to the base body portion 112. For example, the base connecting portion may include first and second base connecting portions 114 and 116 connected to the base body portion 112. Herein, the first and second base connecting portions 114 and 116 may protrude from the base body portion 112 to correspond to each other.

The work plate 120 is spaced apart from the base plate 100 to face the base plate 100. The work plate 120 may include a work body portion 122 corresponding to the base body portion 112, and at least one work connecting portion connected to the work body portion 122 to correspond to the base connecting portion. For example, the work connecting portion may include first and second work connecting portions 124 and 126 connected to the work body portion 122 to correspond to the first and second base connecting portions 114 and 116, respectively. Herein, the first and second work connecting portions 124 and 126 may protrude from the work body portion 122 to correspond to each other.

In addition, the work plate 120 may further include a mount connecting portion 128 connected to the work body portion 122 and providing a mount space. The mount connecting portion 128 may be formed protruding from the work body portion 122 and disposed at a position corresponding to the work connecting portion. For example, the mount connecting portion 128 may be disposed at a position facing one of the first and second work connecting portions 124 and 126.

The surgical mount 130 is mounted on the mount connecting portion 128 to fix the surgical unit. Particularly, one end of the surgical mount 130 is fixedly coupled to the mount connecting portion 128, and another end of the surgical mount 130 may have a fixing means for fixing the surgical unit, for example, a fixing hole. Herein, the surgical unit may be a surgical needle or a surgical drill that is inserted and fixed in the fixing hole.

The main fixing shaft module 140 is disposed between the base body portion 112 and the work body portion 122, and coupled to the work body portion 122 such that the work body portion 122 is rotatable.

The horizontal movement module M is disposed between the main fixing shaft module 140 and the base body portion 112, and moves the main fixing shaft module 140 along first and second directions intersecting each other. For example, the horizontal movement module M may include first and second sliding modules 150 and 160.

The first sliding module 150 is disposed between the main fixing shaft module 140 and the base body portion 112, and moves the main fixing shaft module 140 along one direction of the first and second directions. The second sliding module 160 is disposed between the main fixing shaft module 140 and the first sliding module 150, and moves the main fixing shaft module 140 along the other direction of the first and second directions.

The angle-controlling module is coupled to the base connecting portion such that the base connecting portion is rotatable, coupled to the working connecting portion such that the working connecting portion is rotatable, and allows translational motion between the base connecting portion and the work connecting portion. For example, the angle-controlling module may include first and second angle-controlling modules 170 and 180.

The first angle-controlling module 170 is coupled to the first base connecting portion 114 such that the first base connecting portion 114 is rotatable, coupled to the first work connecting portion 124 such that is the first work connecting portion 124 is rotatable, and allows translational motion between the first base connecting portion 114 and the first work connecting portion 124. The second angle-controlling module 180 is coupled to the second base connecting portion 116 such that the second base connecting portion 116 is rotatable, coupled to the second work connecting portion 126 such that the second work connecting portion 126 is rotatable, and allows translational motion between the second base connecting portion 116 and the second work connecting portion 126.

In the present embodiment, the first base connecting portion 114 may be connected to the base body portion 112 in the one direction of the first and second directions, and the second base connecting portion 116 may be connected to the base body portion 112 in the other direction of the first and second directions. Also, the first work connecting portion 124 may be connected to the work body portion 122 in the one direction, and the second work connecting portion 126 may be connected to the work body portion 122 in the other direction. Herein, the first and second directions may perpendicularly intersect each other.

Hereinafter, the main fixing shaft module 140 will be described in detail.

Figure 6:
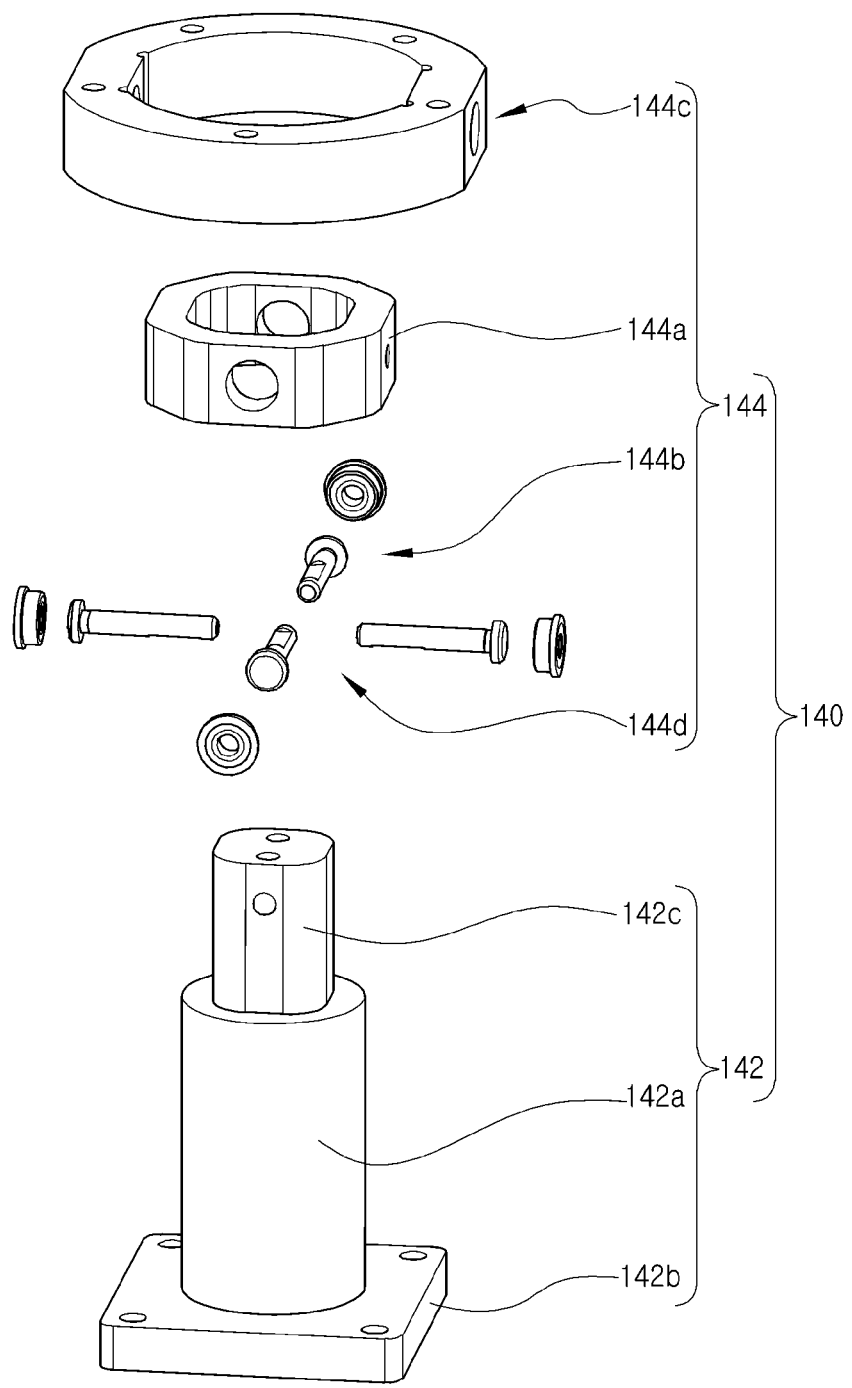
FIG. 6 is an exploded perspective view showing a main fixing shaft module of the parallel-type micro robot in FIG. 2.

FIG. 6 is an exploded perspective view showing a main fixing shaft module of the parallel-type micro robot in FIG. 2.

Referring to FIG. 6, the main fixing shaft module 140 may include a main fixing shaft unit 142 and a main rotational motion connecting unit 144.

The main fixing shaft unit 142 is coupled to the horizontal movement module M and is moved along the first and second directions by the horizontal movement module M. Particularly, the main fixing shaft unit 142 may include a fixing shaft body portion 142a, a bottom connecting portion 142b, and a top connecting portion 142c.

The fixing shaft body portion 142a is disposed along a third direction substantially perpendicular to a horizontal plane substantially parallel to the first and second directions. The bottom connecting portion 142b is connected to a lower portion of the fixing shaft body portion 142a, and is fixedly coupled to the horizontal movement module M, i.e., the second sliding module 160. The top connecting portion 142c is connected to an upper portion of the fixing shaft body portion 142a and coupled to the main rotational motion connecting unit 144.

The main rotational motion connecting unit 144 connects the main fixing shaft unit 142 and the work body portion 122 to allow rotational motion of the work body portion 122. For example, the main rotational motion connecting unit 144 may be a two-axis rotational motion connecting unit such as a universal joint, or an all-round rotational motion connecting unit such as a ball joint.

In the figure, an example of employing the two-axis rotational motion connecting unit as the main rotational motion connecting unit 144 is shown. Particularly, for example, the main rotational motion connecting unit 144 may include a rotating ring plate 144a, a first rotating shaft connecting portion 144b, a fixing ring plate 144c, and a second rotating shaft connecting portion 144d.

A through-hole is formed through the rotating ring plate 144a such that a top connecting portion 142c of the main fixing shaft unit 142 may be inserted. The first rotating shaft connecting portion 144b connects the rotating ring plate 144a and the top connecting portion 142c such that the rotating ring plate 144a is rotated in one direction of the first and second directions.

A through-hole is formed through the fixing ring plate 144c such that the rotating ring plate 144a is inserted. The second rotating shaft connecting portion 144d connects the rotating ring plate 144a and the fixing ring plate 144c such that the rotating ring plate 144a is rotated along the other direction of the first and second directions.

The fixing ring plate 144c is attached and fixed to the lower surface of the work body portion 122. Herein, a rotation through-hole 122a may be formed through the work body portion 122 such that the rotating ring plate 144a may be freely rotated along the first and second directions.

Meanwhile, the rotating ring plate 144a may be directly inserted into the rotation through-hole 122a of the work body portion 122, and coupled by the second rotating shaft connecting portion 144d to rotate along the other direction. As a result, the fixing ring plate 144c may be omitted.

Hereinafter, the first sliding module 150 will be described in detail.

Figure 7:
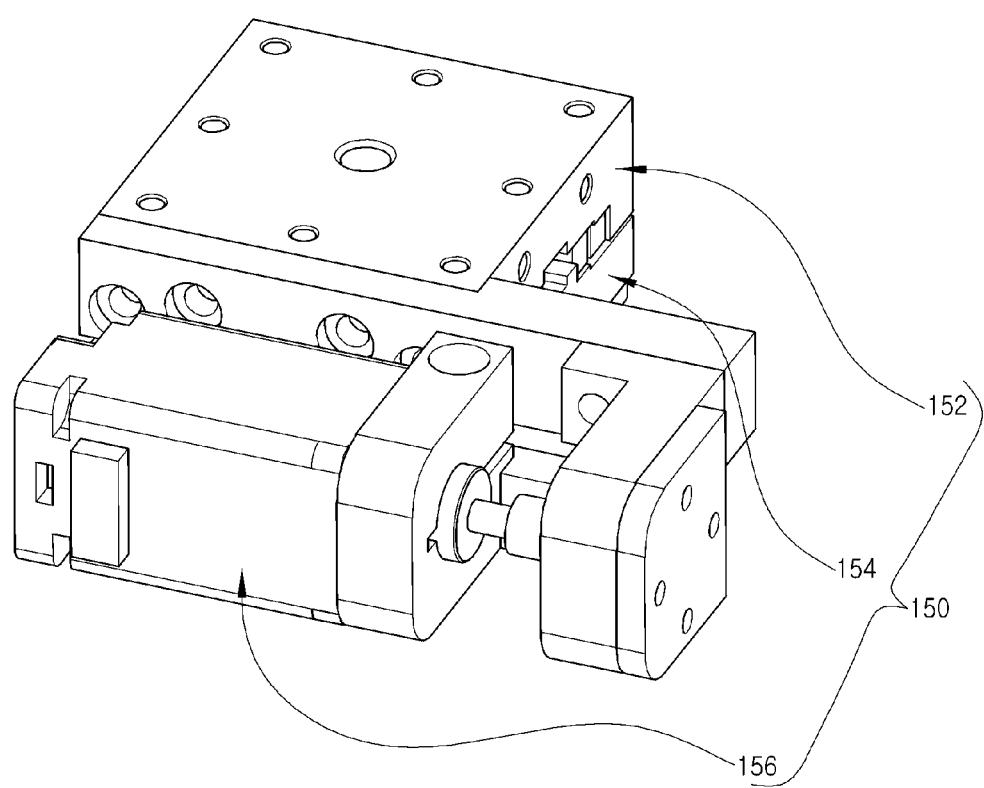
FIG. 7 is a perspective view showing a first sliding module of the parallel-type micro robot in FIG. 2.
Figure 8:
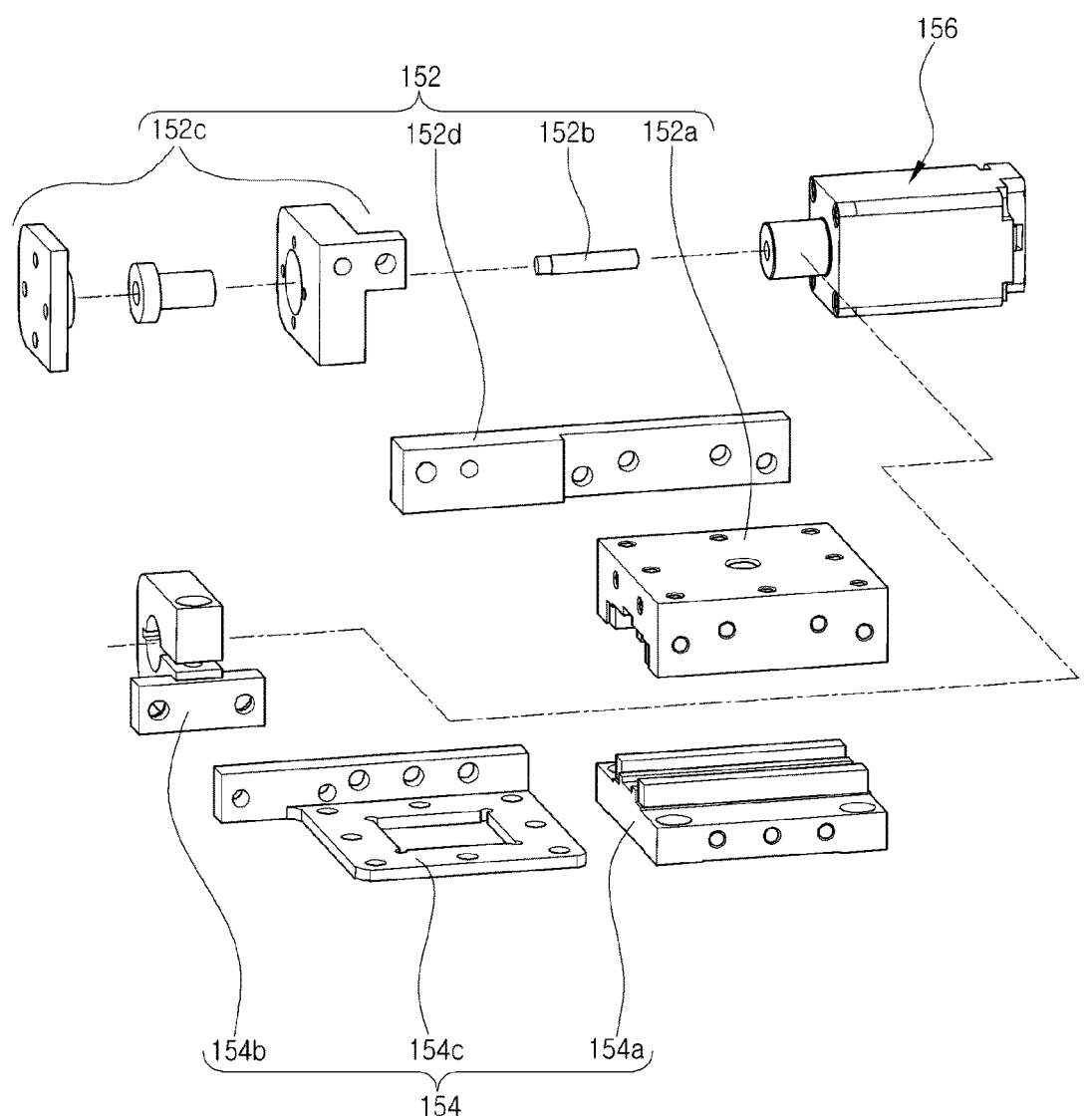
FIG. 8 is an exploded perspective view showing the first sliding module in FIG. 7.

FIG. 7 is a perspective view showing a first sliding module of the parallel-type micro robot in FIG. 2. FIG. 8 is an exploded perspective view showing the first sliding module in FIG. 7.

Referring to FIGS. 7 and 8, the first sliding module 150 may include a first upper sliding unit 152, a first lower sliding unit 154, and a first sliding actuator 156.

The first upper sliding unit 152 is engaged with the first lower sliding unit 154 and may be slidingly moved in one direction of the first and second directions by the power provided by the first sliding actuator 156. That is, the first upper sliding unit 152 may move relative to the first lower sliding unit 154 along the one direction.

More particularly, for example, the first upper sliding unit 152 may include a first upper sliding body portion 152a, a first sliding moving shaft 152b performing translational motion according to the power provided by the first sliding actuator 156, a first sliding moving shaft fixing portion 152c coupled to the first sliding moving shaft 152b, and a first upper sliding connecting portion 152d transmitting the translational motion of the first sliding moving shaft 152b to the first upper sliding body portion 152a by connecting the first sliding moving shaft fixing portion 152c and the first upper sliding body portion 152a In addition, the first lower sliding unit 154 may include a first lower sliding body portion 154a engaged with the first upper sliding body portion 152a, a first sliding actuator fixing portion 154b engaging and fixing a head portion of the first sliding actuator 156, and a first lower sliding connecting portion 154c connecting the first sliding actuator fixing portion 154b and the first lower sliding body portion 154a.

In the present embodiment, in order that the first upper sliding body portion 152a is relatively moved along the one direction with respect to the first lower sliding body portion 154a, one of a sliding rail and a sliding rail groove may be formed on the lower surface of the first upper sliding body portion 152a, and the other of the sliding rail and the sliding rail groove may be formed on the upper surface of the lower sliding body portion 154a. In the figure, for example, a sliding rail groove is formed on the lower surface of the first upper sliding body portion 152a, and a sliding rail is formed on the upper surface of the first lower sliding body portion 154a.

Meanwhile, although not shown in the drawings, the second sliding module 160 may include a second upper sliding unit, a second lower sliding unit, and a second sliding actuator. Herein, the second upper sliding unit is engaged with the second lower sliding unit, and may be slidingly moved in the other direction of the first and second directions by the power provided by the second sliding actuator.

In the present embodiment, the second sliding module 160 has substantially the same components as the corresponding first sliding module 150 except for moving direction of sliding. Thus, any further detailed description will be omitted.

Hereinafter, the first angle-controlling module 170 will be described in detail.

Figure 9:
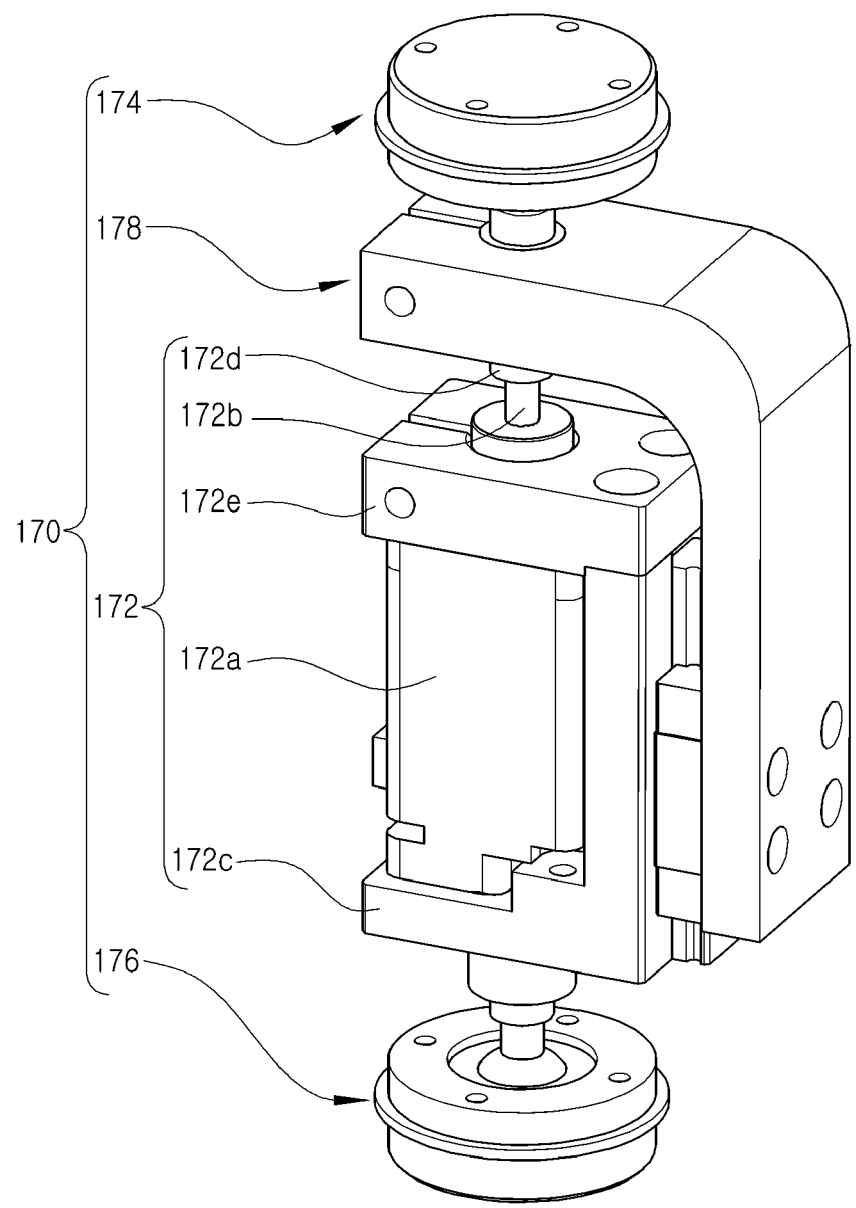
FIG. 9 is a perspective view showing a first angle-controlling module of the parallel-type micro robot in FIG. 2.
Figure 10:
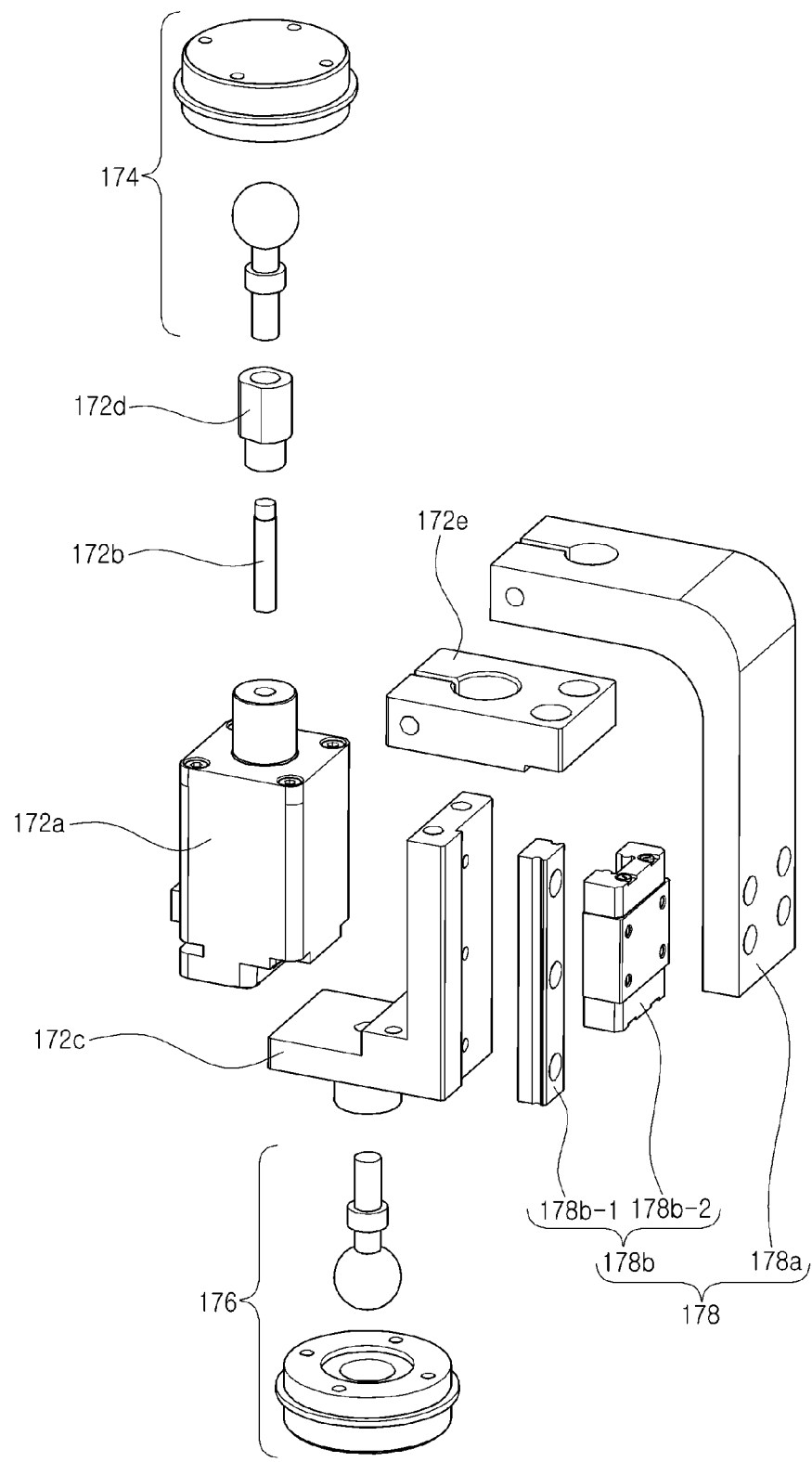
FIG. 10 is an exploded perspective view showing the first angle-controlling module in FIG. 9.

FIG. 9 is a perspective view showing a first angle-controlling module of the parallel-type micro robot in FIG. 2. FIG. 10 is an exploded perspective view showing the first angle-controlling module in FIG. 9.

Referring to FIGS. 9 and 10, the first angle-controlling module 170 may include a first translational motion unit 172, a first one-side rotational motion connecting unit 174, a first another-side rotational motion connecting unit 176 and a first up-down movement guide unit 178.

The first translational motion unit 172 allows translational motion between the first base connecting portion 114 and the first work connecting portion 124. That is, the first translational motion unit 172 may increase or decrease a gap between the first base connecting portion 114 and the first work connecting portion 124, so that an angle of the work plate 120 may be changed.

Particularly, for example, the first translational motion unit 172 may include a first up-down movement actuator 172a, a first up-down moving shaft portion 172b, a first actuator mounting portion 172c, a first up-down moving shaft fixing portion 172d and a first actuator fixing portion 172e.

The first up-down movement actuator 172a is disposed between the first base connecting portion 114 and the first work connecting portion 124, and provides power for translational motion in the third direction.

The first up-down moving shaft portion 172b performs translational motion according to the power of the first up-down movement actuator 172a between the first work connecting portion 124 and the first up-down movement actuator 172a, or between the first base connecting portion 114 and the first up-down movement actuator 172a. In the figure, for example, the first up-down moving shaft portion 172b is disposed between the first work connecting portion 124 and the first up-down movement actuator 172a.

The first actuator mounting portion 172c mounts and secures the first up-down movement actuator 172a. In other words, the first up-down movement actuator may be mounted on the inner side of the first actuator mounting portion 172c, and the first up-down movement guide unit 178 may be coupled to the outer side of the first actuator mounting portion 172c. For example, the first actuator mounting portion 172c may be formed in an L-shape so as to be coupled to the first up-down movement guide unit 178 on the outer side while easily mounting the first up-down movement actuator 172a on the inner side.

The first up-down moving shaft fixing portion 172d is fixed to the first up-down moving shaft portion 172b and connects the first up-down moving shaft portion 172b and the first up-down movement guide unit 178. On the other hand, the first up-down moving shaft fixing portion 172d may be omitted. Herein, the first up-down moving shaft portion 172b may be directly coupled to the first up-down movement guide unit 178 to perform translational motion together with the first up-down movement guide unit 178.

The first actuator fixing portion 172e inserts the head portion of the first up-down movement actuator 172a mounted on the first actuator mounting portion 172c to more firmly fix the head portion. For example, the first actuator mounting portion 172c and the first actuator fixing portion 172e are coupled to each other to form a U-shape, so that the first up-down movement actuator 172a may be more firmly fixed. Meanwhile, the first actuator mounting portion 172c and the first actuator fixing portion 172e may be omitted, and the first up-down movement actuator 172a may be disposed alone.

The first one-side rotational motion connecting unit 174 connects the first base connecting portion 114 and the first translational motion unit 172 to allow rotational motion of the first base connecting portion 114. Particularly, the first one-side rotational motion connecting unit 174 connects the first base connecting portion 114 and the first actuator mounting portion 172c. The first one-side rotational motion connecting unit 174 may be a two-axis rotational motion connecting unit such as a universal joint, or may be an all-round rotational motion connecting unit such as a ball joint. In the figure, for example, the first one-side rotational motion connecting unit 174 is shown employing the all-round rotational motion connecting unit.

The first another-side rotational motion connecting unit 176 connects the first work connecting portion 124 and the first translational motion unit 172 to allow rotational motion of the first work connecting portion 124. Particularly, the first another-side rotational motion connecting unit 176 connects the first work connecting portion 124 and the first up-down moving shaft portion 172b. The first another-side rotational motion connecting unit 176 may be a two-axis rotational motion connecting unit such as a universal joint, or may be an all-round rotational motion connecting unit such as a ball joint. In the figure, for example, the first rotational motion connecting unit 176 is shown employing the all-round rotational motion connecting unit.

The first up-down movement guide unit 178 is coupled to the first translational motion unit 172 to guide translational motion according to the first translational motion unit 172. For example, the first up-down movement guide unit 178 may include a first guide body portion 178a and a first up-down movement sliding portion 178b.

The first guide body portion 178a may be coupled to the first up-down moving shaft portion 172b to perform translational motion with the first up-down moving shaft portion 172b. For example, the first guide body portion 178a may have an L-shape. Herein, an end portion of the L-shape may enclose and secure the first up-down moving shaft fixing portion 172d that is fixed to the first up-down moving shaft portion 172b, and a side portion of the L-shape may be coupled to the first up-down movement sliding portion 178b.

The first up-down movement sliding portion 178b is disposed between the first up-down movement actuator 172a and the first guide body portion 178a, to slide when the first guide body portion 178a performs translational motion along the third direction and guide movement of the first guide body portion 178a. Particularly, the first up-down movement sliding portion 178b may be disposed between an outer surface of the first actuator mounting portion 172c and a side portion of the first guide body portion 178a.

The first up-down movement sliding portion 178b may include a first up-down movement rail portion 178b-1 and a first up-down movement rail groove portion 178b-2.

The first up-down movement rail portion 178b-1 is coupled to one of the outer surface of the first actuator mounting portion 172c and the side portion of the first guide body portion 178a, and the first up-down movement rail groove portion 178b-2 may be coupled to the other of the outer surface of the first actuator mounting portion 172c and the side portion of the first guide body portion 178a. In the figure, for example, the first up-down movement rail portion 178b-1 is coupled to the outer surface of the first actuator mounting portion 172c, and the first up-down movement rail groove portion 178b-2 is coupled to the side portion of the first guide body portion 178a.

Thus, as the first up-down movement rail groove portion 178b-2 is engaged with the first up-down movement rail portion 178b-1, and slides along the first up-down movement rail portion 178b-1. Accordingly, the translational motion of the guide body portion 178a may be stably guided.

Meanwhile, although not shown in the drawings, the second angle-controlling module 180 may include a second translational motion unit, a second one-side rotational motion connecting unit, a second another-side rotational motion connecting unit, and a second up-down movement guide unit.

The second translational motion unit allows translational motion between the second base connecting portion 116 and the second work connecting portion 126. The second one-side rotational motion connecting unit connects the second base connecting portion 116 and the second translational motion unit to allow rotational motion of the second base connecting portion 116. The second another-side rotational motion connecting unit connects the second work connecting portion 126 and the second translational motion unit to allow rotational motion of the second work connecting portion 126. The second up-down movement guide unit is coupled to the second translational motion unit to guide the translational motion according to the second translational motion unit.

In the present embodiment, the second angle-controlling module 180 has substantially the same components as the first angle-controlling module 170 except for disposed positions. Thus, any further detailed description will be omitted.

According to the present embodiment, the parallel-type micro robot 100 includes the first sliding module 150, the second sliding module 160, the first angle-controlling module 170 and the second angle-controlling module 180, and controls translational motion in four directions. Thus, it is possible to implement a parallel-type micro robot having four degrees of freedom to precisely control the angle and position of the work plate 120.

In addition, by controlling the angle of the work plate 120 using the first angle-controlling module 170 and the second angle-controlling module 180, the number of actuators for controlling the angle of the work plate 120 may be greatly reduced as compared with the conventional parallel-type micro robot, and as a result, it is possible to manufacture a small-sized, lightweight structure, thereby minimizing restrictions on installation and operation space.

Further, since each of the first and second angle-controlling modules 170 and 180 has an up-down movement guide unit coupled to an up-down moving shaft portion, translational motion according to the up-down moving shaft portion may be stably guided. In other words, it may be structurally unstable during translational motion since the up-down moving shaft portion is relatively thin, but the up-down movement guide unit may enhance the structural stability by reinforcing the up-down moving shaft portion.

Although the present invention has been described in the detailed description of the invention with reference to exemplary embodiments of the present invention, it will be understood to those skilled in the art that various modifications and variation can be made in the present invention without departing from the spirit or scope of the invention.

The invention claimed is:

1. A parallel-type micro robot comprising:
  a base plate including a base body portion and at least one base connecting portion connected to the base body portion;
  a work plate including a work body portion corresponding to the base body portion and at least one work connecting portion connecting to the work body portion to correspond to the base connecting portion;
  a main fixing shaft module disposed between the base body portion and the work body portion, and coupled to the work body portion such that the work body portion is rotatable;
  a horizontal movement module disposed between the main fixing shaft module and the base body portion, and moving the main fixing shaft module along first and second directions intersecting each other; and at least one angle-controlling module coupled to the base connecting portion such that the base connecting portion is rotatable, coupled to the work connecting portion such that the work connecting portion is rotatable, and allowing translational motion between the base connecting portion and the work connecting portion, wherein the angle-controlling module includes:

a translational motion unit allowing translational motion between the base connecting portion and the work connecting portion;

a one-side rotational motion connecting unit connecting the base connecting portion and the translational motion unit to allow rotational motion of the base connecting portion;

an another-side rotational motion connecting unit connecting the work connecting portion and the translational motion unit to allow rotational motion of the work connecting portion; and an up-down movement guide unit coupled to the translational motion unit to guide translational motion according to the translational motion unit.

2. The parallel-type micro robot of claim 1, wherein the base connecting portion includes first and second base connecting portions connected to the base body portion, the work connecting portion includes first and second work connecting portions connected to the work body portion to correspond to the first and second base connecting portions, respectively, and wherein the angle-controlling module includes:

a first angle-controlling module coupled to the first base connecting portion such that the first base connecting portion is rotatable, coupled to the first work connecting portion such that the first work connecting portion is rotatable, and allowing translational motion between the first base connecting portion and the first work connecting portion; and a second angle-controlling module coupled to the second base connecting portion such that the second base connecting portion is rotatable, coupled to the second work connecting portion such that the second work connecting portion is rotatable, and allowing translational motion between the second base connecting portion and the second work connecting portion.

3. The parallel-type micro robot of claim 2, wherein the first base connecting portion is connected to the base body portion in one direction of the first and second directions, the second base connecting portion is connected to the base body portion in the other direction of the first and second directions, the first work connecting portion is connected to the work body portion in the one direction, and the second work connecting portion is connected to the work body portion in the other direction.

4. The parallel-type micro robot of claim 3, wherein the first and second directions perpendicularly intersect each other.

5. The parallel-type micro robot of claim 1, wherein the work plate further includes a mount connecting portion connected to the work body portion and providing a mount space.

6. The parallel-type micro robot of claim 5, wherein the mount connecting portion is disposed at a location corresponding to the work connecting portion.

7. The parallel-type micro robot of claim 5, further comprising a surgical mount coupled to the mount connecting portion, wherein a surgical unit is mountable on the surgical mount.

8. The parallel-type micro robot of claim 1, wherein the translational motion unit includes:

an up-down movement actuator providing power for translational motion; and an up-down moving shaft portion performing translational motion according to the power of the up-down movement actuator between the work connecting portion and the up-down movement actuator, or between the base connecting portion and the up-down movement actuator.

9. The parallel-type micro robot of claim 8, wherein the up-down movement guide unit includes:

a guide body portion coupled to the up-down moving shaft portion to perform translational motion with the up-down moving shaft portion; and an up-down movement sliding portion disposed between the up-down movement actuator and the guide body portion to slide and guide the guide body portion when the guide body portion performs translational motion.

10. The parallel-type micro robot of claim 9, wherein the translational motion unit further includes an actuator mounting portion having an inner face on which the up-down movement actuator is mounted and an outer face coupled to the up-down movement sliding portion.

11. The parallel-type micro robot of claim 9, wherein the up-down movement sliding portion includes:

an up-down movement rail portion coupled to one of the up-down movement actuator and the guide body portion; and an up-down movement rail groove portion coupled to the other of the up-down movement actuator and the guide body portion to slide along the up-down movement rail portion.

12. The parallel-type micro robot of claim 1, wherein the horizontal movement module includes:

a first sliding module disposed between the main fixing shaft module and the base body portion to move the main fixing shaft module along one direction of the first and second directions; and a second sliding module disposed between the main fixing shaft module and the first sliding module to move the main fixing shaft module along the other direction of the first and second directions.

13. The parallel-type micro robot of claim 1, wherein the main fixing shaft module includes:

a main fixing shaft unit coupled to the horizontal movement module to be moved along the first and second directions by the horizontal movement module; and a main rotational motion connecting unit connecting the main fixing shaft unit and the work body portion to allow rotational motion of the work body portion.

14. A surgical robot system comprising:

a parallel-type micro robot; and a robot installation stage on which the parallel-type micro robot is installed corresponding to an operating table on which a patient is disposed, wherein the parallel-type micro robot comprises:

a base plate installed on the robot installation stage, and including a base body portion and at least one base connecting portion connected to the base body portion;

a work plate including a work body portion corresponding to the base body portion and at least one work connecting portion connecting to the work body portion to correspond to the base connecting portion;

a main fixing shaft module disposed between the base body portion and the work body portion, and coupled to the work body portion such that the work body portion is rotatable;

a horizontal movement module disposed between the main fixing shaft module and the base body portion, and moving the main fixing shaft module along first and second directions intersecting each other; and at least one angle-controlling module coupled to the base connecting portion such that the base connecting portion is rotatable, coupled to the work connecting portion such that the work connecting portion is rotatable, and allowing translational motion between the base connecting portion and the work connecting portion, wherein the angle-controlling module includes:

a translational motion unit allowing translational motion between the base connecting portion and the work connecting portion;

a one-side rotational motion connecting unit connecting the base connecting portion and the translational motion unit to allow rotational motion of the base connecting portion;

an another-side rotational motion connecting unit connecting the work connecting portion and the translational motion unit to allow rotational motion of the work connecting portion; and an up-down movement guide unit coupled to the translational motion unit to guide translational motion according to the translational motion unit.

15. The surgical robot system of claim 14, wherein the robot installation stage includes:

a robot-installed part on which the parallel-type micro robot is installed;

a one-directional moving part coupled to the robot-installed part to move the robot-installed part in one-direction crossing over the operating table; and a pair of another-directional moving parts respectively disposed at both sides of the operating table to be coupled to the one-directional moving part, to move the one-directional moving part along another-direction intersecting the one-direction.

* * * * *